(12) United States Patent  
Wendland et al.

(10) Patent No.: US 11,752,264 B2  
(45) Date of Patent: Sep. 12, 2023

(54) AUTO-INJECTOR DEVICE

(71) Applicant: SANOFI-AVENTIS DEUTSCHLAND GMBH, Frankfurt am Main (DE)

(72) Inventors: Stefan Wendland, Frankfurt am Main (DE); Michael Harms, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 206 days.

(21) Appl. No.: 17/099,707

(22) Filed: Nov. 16, 2020

(65) Prior Publication Data  
US 2021/0077724 A1 Mar. 18, 2021

Related U.S. Application Data

(63) Continuation of application No. 15/779,068, filed as application No. PCT/EP2016/078243 on Nov. 21, 2016, now Pat. No. 11,058,819.

(30) Foreign Application Priority Data

Nov. 27, 2015 (EP) ..................................... 15196668

(51) Int. Cl.  
*A61M 5/20* (2006.01)  
*A61M 5/142* (2006.01)

(52) U.S. Cl.  
CPC ...... *A61M 5/2033* (2013.01); *A61M 5/14248* (2013.01); *A61M 5/20* (2013.01); *A61M 2005/2086* (2013.01); *A61M 2205/0266* (2013.01); *A61M 2205/364* (2013.01)

(58) Field of Classification Search  
CPC .. A61M 5/2033; A61M 5/14248; A61M 5/20; A61M 2005/2086; A61M 2205/0266; A61M 2205/364  
See application file for complete search history.

(56) References Cited

U.S. PATENT DOCUMENTS

| | | | |
|---|---|---|---|
| 4,518,384 A | * | 5/1985 | Tarello ...................... F41A 9/84 604/61 |
| 4,899,910 A | | 2/1990 | Tabei et al. |

(Continued)

FOREIGN PATENT DOCUMENTS

| | | |
|---|---|---|
| CN | 101184523 | 5/2008 |
| CN | 102836478 | 12/2012 |

(Continued)

OTHER PUBLICATIONS

PCT International Preliminary Report on Patentability in International Appln. No. PCT/EP2016/078243, dated May 29, 2018, 7 pages.

(Continued)

*Primary Examiner* — Lauren P Farrar  
(74) *Attorney, Agent, or Firm* — Fish & Richardson P.C.

(57) ABSTRACT

An auto-injector device comprises a stopper for expelling a medicament out of a medicament reservoir; a driving element which has a first configuration and a second configuration and is configured to change shape from the first configuration to the second configuration when the temperature of the driving element is raised above a shape change temperature, so as to drive the stopper of the syringe mechanism through the medicament reservoir; and a heating mechanism configured to actively heat the driving element. The heating mechanism is a chemical heating element configured to generate heat through an exothermic process or comprises a fluid reservoir for retaining a fluid; a heater configured to heat the fluid in the fluid reservoir; a pump configured to expel the fluid out of the fluid reservoir; and a connecting conduit arranged to carry the fluid from the fluid reservoir to the driving element.

20 Claims, 4 Drawing Sheets

(56) References Cited

U.S. PATENT DOCUMENTS

| | | | |
|---|---|---|---|
| 8,021,357 B2 | 9/2011 | Tanaka et al. | |
| 8,387,612 B2 | 3/2013 | Damani et al. | |
| 2001/0016710 A1 | 8/2001 | Nason et al. | |
| 2002/0004639 A1 | 1/2002 | Willis et al. | |
| 2011/0257622 A1* | 10/2011 | Salahieh | A61M 25/0075 604/246 |
| 2015/0045763 A1* | 2/2015 | Barone, Jr. | A61J 1/16 604/408 |
| 2018/0220708 A1 | 8/2018 | Scott et al. | |

FOREIGN PATENT DOCUMENTS

| | | |
|---|---|---|
| CN | 103316398 | 9/2013 |
| JP | S62-121877 | 6/1987 |
| JP | H4-105660 | 4/1992 |
| JP | H04-200565 | 7/1992 |
| JP | H05-168680 | 7/1993 |
| JP | H05-212093 | 8/1993 |
| JP | 2005-530565 | 10/2005 |
| WO | WO 2004/000395 | 12/2003 |
| WO | WO 2006/126653 | 11/2006 |
| WO | WO 2008/057223 | 5/2008 |
| WO | WO 2014/143770 | 9/2014 |

OTHER PUBLICATIONS

PCT International Search Report and Written Opinion in International Appln. No. PCT/EP2016/0787243, dated Feb. 27, 2017, 11 pages.

* cited by examiner

AUTO-INJECTOR DEVICE

CROSS REFERENCE TO RELATED APPLICATIONS

The present application is a continuation of U.S. patent application Ser. No. 15/779,068, filed May 24, 2018, which is the national stage entry of International Patent Application No. PCT/EP2016/078243, filed on Nov. 21, 2016, and claims priority to Application No. EP 15196668.6, filed on Nov. 27, 2015, the disclosures of which are expressly incorporated herein in entirety by reference thereto.

FIELD

The present disclosure relates to an auto-injector device.

BACKGROUND

Injection devices, such as auto-injectors, are known in the art for dispensing a medicament to an injection site of a user. Such injection devices typically comprise a body and a cap. A needle syringe is located in the body. The cap is removably attached to the body to shield the needle of the needle syringe. To dispense the medicament, the cap is first removed from the body to expose the needle. The needle is then inserted into the body of the user at the injection site to dispense the medicament.

SUMMARY

According to an embodiment, an auto-injector device is provided, including a medicament reservoir, a stopper for expelling a medicament out of the medicament reservoir, a driving element, formed from a shape memory alloy, which has a first configuration and a second configuration and is configured to change shape from the first configuration to the second configuration when the temperature of the driving element is raised above a shape change temperature, so as to drive the stopper of the syringe mechanism through the medicament reservoir, and a heating mechanism configured to actively heat the driving element, wherein the heating mechanism is a chemical heating element configured to generate heat through an exothermic process.

The first configuration of the driving element may be a compressed coil shape. The second configuration of the driving element may be an expanded coil shape.

The exothermic process may be an exothermic crystallisation of a supersaturated solution.

The exothermic process may be an exothermic rehydration of a dehydrated salt.

The exothermic process may be an exothermic chemical reaction between a first chemical and a second chemical.

The chemical heating element may include a first chamber containing the first chemical, a second chamber containing the second chemical, and a frangible membrane (143) arranged to separate the first chemical from the second chemical.

The shape memory alloy may be a nickel-titanium alloy.

The auto-injector device may include a medicament which is retained in the medicament reservoir and is arranged to be expelled from the medicament reservoir by the stopper.

According to another aspect, an auto-injector device is provided, including a medicament reservoir, a stopper for expelling a medicament out of the medicament reservoir, a driving element, formed from a shape memory alloy, which has a first configuration and a second configuration and is configured to change shape from the first configuration to the second configuration when the temperature of the driving element is raised above a shape change temperature, so as to drive the stopper of the syringe mechanism through the medicament reservoir, and a heating mechanism configured to actively heat the driving element, the heating mechanism including a fluid reservoir for retaining a fluid, a heater configured to heat the fluid in the fluid reservoir, a pump configured to expel the fluid out of the fluid reservoir, and a connecting conduit arranged to carry the fluid from the fluid reservoir to the driving element.

The first configuration of the driving element may be a compressed coil shape. The second configuration of the driving element may be an expanded coil shape.

The driving element may be disposed in a proximal end of the medicament reservoir. The connecting tube may be configured to fill the proximal end of the medicament reservoir with the fluid.

The shape memory alloy may be a nickel-titanium alloy.

The auto-injector device may include a medicament which is retained in the medicament reservoir and is arranged to be expelled from the medicament reservoir by the stopper.

According to another aspect, a method of operating an injection device is provided, including heating a driving element formed from a shape memory alloy, using a chemical heating element configured to generate heat through an exothermic process. The driving element has a first configuration and a second configuration and is configured to change shape from the first configuration to the second configuration when the temperature of the driving element is raised above a shape change temperature, so as to drive a stopper through a medicament reservoir and expel a medicament out of the medicament reservoir.

According to another aspect, a method of operating an injection device is provided, including heating a driving element formed from a shape memory alloy, by: heating a fluid retained in a fluid reservoir; and pumping the fluid out of the fluid reservoir to the driving element through a connecting conduit. The driving element has a first configuration and a second configuration and is configured to change shape from the first configuration to the second configuration when the temperature of the driving element is raised above a shape change temperature, so as to drive a stopper through a medicament reservoir and expel a medicament out of the medicament reservoir.

These and other aspects will be apparent from and elucidated with reference to the embodiments described hereinafter.

BRIEF DESCRIPTION OF THE FIGURES

Embodiments of the invention will now be described, by way of example only, with reference to the accompanying drawings, in which.

DETAILED DESCRIPTION

Figure 1A:
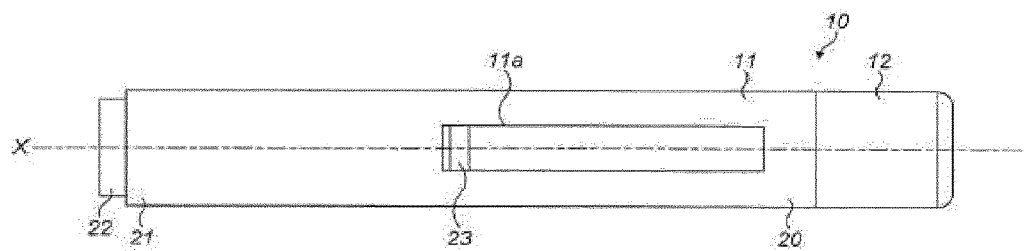
FIG. 1A is a schematic side view of an auto-injector device according to an exemplary embodiment, with a cap attached to a body of the injection device.

One or more embodiments provide an improved dispense mechanism for an auto-injector device, wherein the dispense mechanism includes a driving element formed from a shape memory alloy. The shape memory alloy changes configuration when the temperature is raised above a threshold by active heating, which is used to provide an expanding driving element for the dispense mechanism. In addition, using a heating arrangement to raise the temperature of the driving element can aid with warming the medicament prior to injection.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 5 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1B:
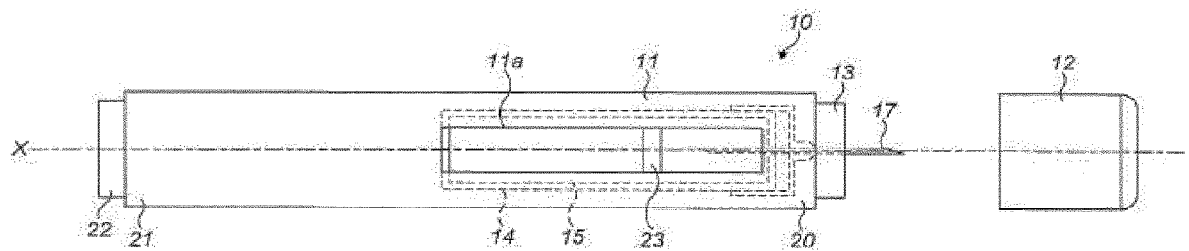
FIG. 1B is a schematic side view of the auto-injector device of FIG. 1A, with the cap removed from the body.

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically a user must remove cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to housing 11 to permit movement of sleeve 13 relative to housing 11. For example, sleeve 13 can move in a longitudinal direction parallel to longitudinal axis X. Specifically, movement of sleeve 13 in a proximal direction can permit a needle 17 to extend from distal region 20 of housing 11.

Insertion of needle 17 can occur via several mechanisms. For example, needle 17 may be fixedly located relative to housing 11 and initially be located within an extended needle sleeve 13. Proximal movement of sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 13.

Another form of insertion is "automated," whereby needle 17 moves relative to housing 11. Such insertion can be triggered by movement of sleeve 13 or by another form of activation, such as, for example, a button 22. As shown in FIGS. 1A & 1B, button 22 is located at a proximal end of housing 11. However, in other embodiments, button 22 could be located on a side of housing 11.

Other manual or automated features can include drug injection or needle retraction, or both. Injection is the process by which a bung or piston 23 is moved from a proximal location within a syringe (not shown) to a more distal location within the syringe in order to force a medicament from the syringe through needle 17. In some embodiments, a drive spring (not shown) is under compression before device 10 is activated. A proximal end of the drive spring can be fixed within proximal region 21 of housing 11, and a distal end of the drive spring can be configured to apply a compressive force to a proximal surface of piston 23. Following activation, at least part of the energy stored in the drive spring can be applied to the proximal surface of piston 23. This compressive force can act on piston 23 to move it in a distal direction. Such distal movement acts to compress the liquid medicament within the syringe, forcing it out of needle 17.

Following injection, needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of sleeve 13 has moved past a distal end of needle 17, and needle 17 is covered, sleeve 13 can be locked. Such locking can include locking any proximal movement of sleeve 13 relative to housing 11.

Another form of needle retraction can occur if needle 17 is moved relative to housing 11. Such movement can occur if the syringe within housing 11 is moved in a proximal direction relative to housing 11. This proximal movement can be achieved by using a retraction spring (not shown), located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 22 or other components of device 10 can be locked as required.

Figure 2:
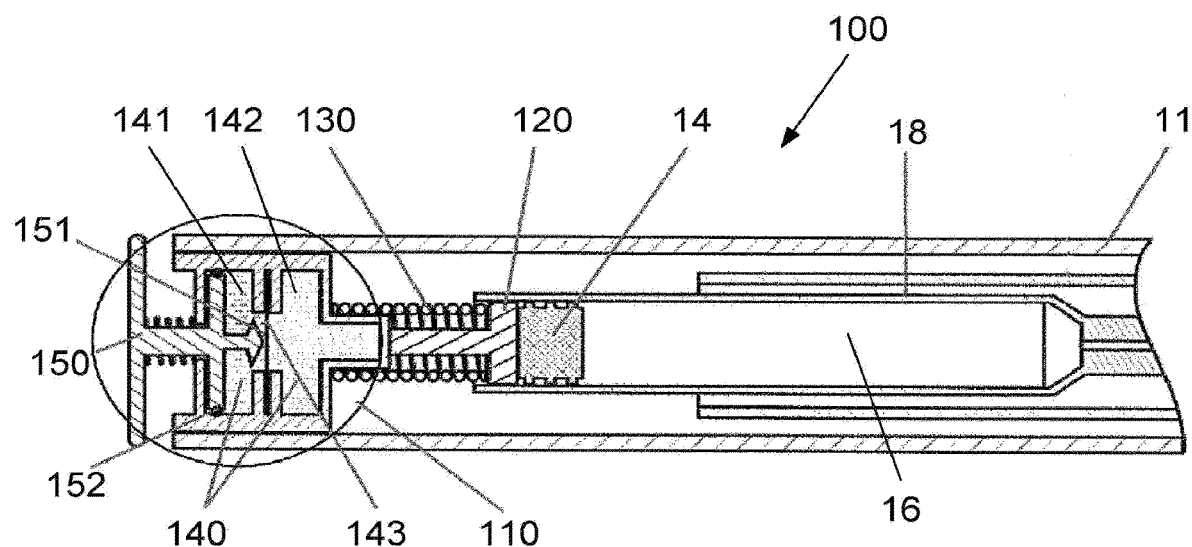
FIG. 2 is a schematic cross-sectional side view of the FIGS. 1A and 1B auto-injector device according to an exemplary embodiment.

With reference to FIG. 2, an injection device 100 according to a first embodiment is shown. The injection device 100 comprises a syringe 18 containing liquid medicament 16, substantially as described with respect to FIGS. 1a and 1b, and a dispense mechanism 110 configured to displace the rubber stopper 23 of the syringe 18 toward the distal end of the medicament chamber.

The dispense mechanism 110 comprises a piston 120, a driving element 130, a heating mechanism 140 and a dispense button 150. The piston 120 is coupled to the rubber stopper 14 of the syringe 18, and the driving element 130 is disposed between the piston 120 and the heating mechanism 140 at the proximal end of the injector housing. The driving element 130 is mechanically coupled to a shoulder of the piston 120 at a distal end of the driving element 130 and is fixed to a reaction surface at a proximal end of the driving element 130.

The driving element 130 is formed from a shape memory alloy (SMA) such as, for example, nickel titanium or copper aluminium nickel. A shape memory alloy may also be referred to as a memory metal or smart metal. The SMA forms a driving element 130 having a first configuration, which is a compressed coil shape, and a second configuration, which is an expanded coil shape. Due to the properties of the SMA, the driving element 130 remains in the first configuration when the temperature is below a threshold temperature. As the temperature of the driving element 130 rises above the threshold, the driving element 130 changes from the first configuration to the second configuration.

The second configuration of the driving element 130 is set by working the SMA at a very high temperature to form the required shape for the driving element 130 in the second configuration. The SMA is cooled rapidly, which sets the formed shape of the driving element 130 as the second configuration. The SMA can be further worked when below the threshold temperature in order to set the shape for the driving element 130 in the first configuration. The SMA remains in the first configuration until the temperature of the driving element 130 rises above the threshold.

The expanded coil shape of the second configuration has a greater length than the compressed coil shape of the first configuration. When the temperature of the driving element 130 rises above the threshold the shape of the driving element 130 changes from a compressed coil shape to an expanded coil shape and therefore the length of the driving element 130 increases. The expansion of the driving element 130 exerts an axial force on the piston 120, which displaces the rubber stopper 23 of the syringe 18 towards the distal end of the medicament chamber. The change in configuration of the driving element 130 therefore causes the medicament 16 to be dispensed through the needle of the syringe 18.

The heating mechanism 140 of the dispense mechanism 110 is configured to raise the temperature of the driving element 130 when the dispense mechanism 110 is activated. The heating mechanism 140 is arranged at a proximal end of the injector body 11 and comprises a first proximal chamber 141 and a second distal chamber 142 which are separated by a frangible membrane 143. The first chamber 141 and the second chamber 142 are connected by a narrow aperture, over which the membrane 143 is placed.

The first proximal chamber 141 contains a first chemical and the second distal chamber 142 comprises a second chemical. The first chemical and second chemical are in a fluid form and, when mixed, the chemicals react exothermically and generate heat. When the membrane 143 of the heating mechanism 140 is ruptured the first chemical is mixed with the second chemical to generate heat and raise the temperature of the driving element 130. The second distal chamber 142 comprises a protruding portion which is arranged to extend through a central region of the coil shaped driving element 130, so as to improve the heat coupling between the heating mechanism 140 and the driving element 130.

The dispense button 150 is arranged to protrude from the proximal end of the injector body 11, and can be pushed axially towards the injector body 11 in order to activate the dispense mechanism 110. The dispense button 150 extends through the proximal end of the injector body 11 into the interior thereof, with the distal end of the dispense button 150 disposed within the first chamber 141 of the heating mechanism 140. The distal end of the dispense button 150 comprises a piercing element 151 extending axially towards a distal end of the first chamber 141 of the heating mechanism 140, and a stopper element 152 having a cross section which substantially matches an internal cross section of the first chamber 141 of the heating mechanism 140.

Figure 3:
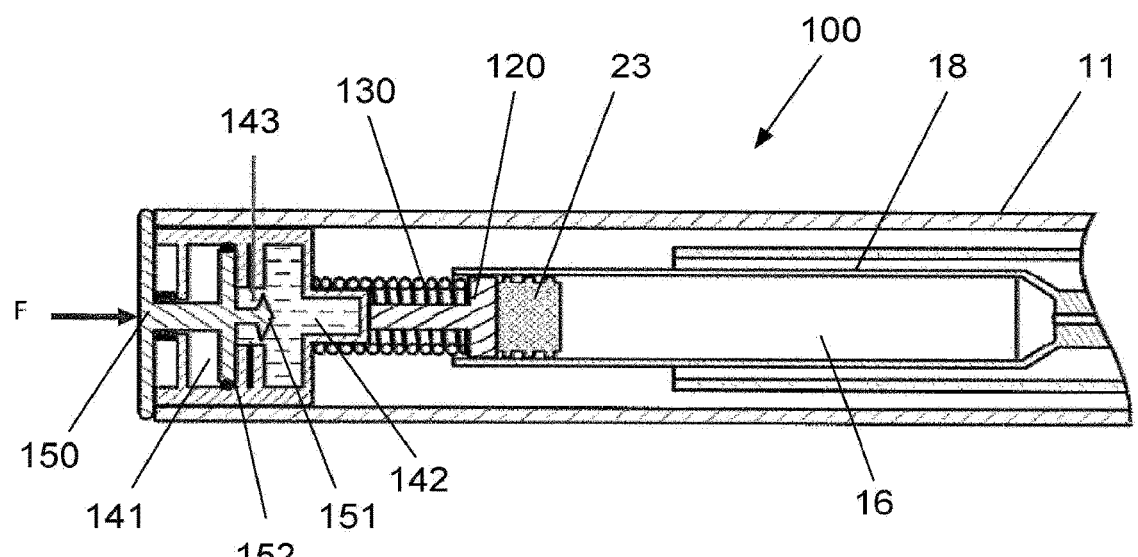
FIG. 3 is a schematic cross-sectional side view of the auto-injector device of FIG. 2.

FIG. 3 shows the injection device 100 of the first embodiment in an intermediate state wherein the dispense button 150 is pushed axially towards the injector body 11. The piercing element 151 is displaced towards a distal end of the device 100 when the dispense button 150 is pushed, and is arranged to pierce the membrane 143 between the first chamber 141 and the second chamber 142 of the heating mechanism 140. Additionally, the stopper element 152 is displaced from the proximal end of the first chamber 141 to the distal end of the first chamber 141, such that substantially all of the first chemical is displaced into the second chamber 142 through the membrane 143.

The first chemical is displaced into the second chamber 142 of the heating mechanism 140 and mixed with the second chemical, which causes an exothermic chemical reaction and generates heat. The temperate of the driving element 130, at least a portion of which surrounds the protruding portion of the second chamber 142 of the heating mechanism 140, is raised above the threshold temperature.

The protruding portion of the second chamber 142 is arranged to extend through the driving element 130. The protruding portion improves the transfer of heat from the heating mechanism 140 to the driving element 130. The protruding portion may extend along a part of, of the entire length of, the driving element 130. Alternatively, or in addition, the protruding portion of the second chamber 142 may extend around the outside of the driving element 130. The second chamber 142 and, in particular, the protruding portion thereof, may be formed from a metallic or ceramic material to improve the transfer of heat from the heating mechanism 140 to the driving element 130.

Figure 4:
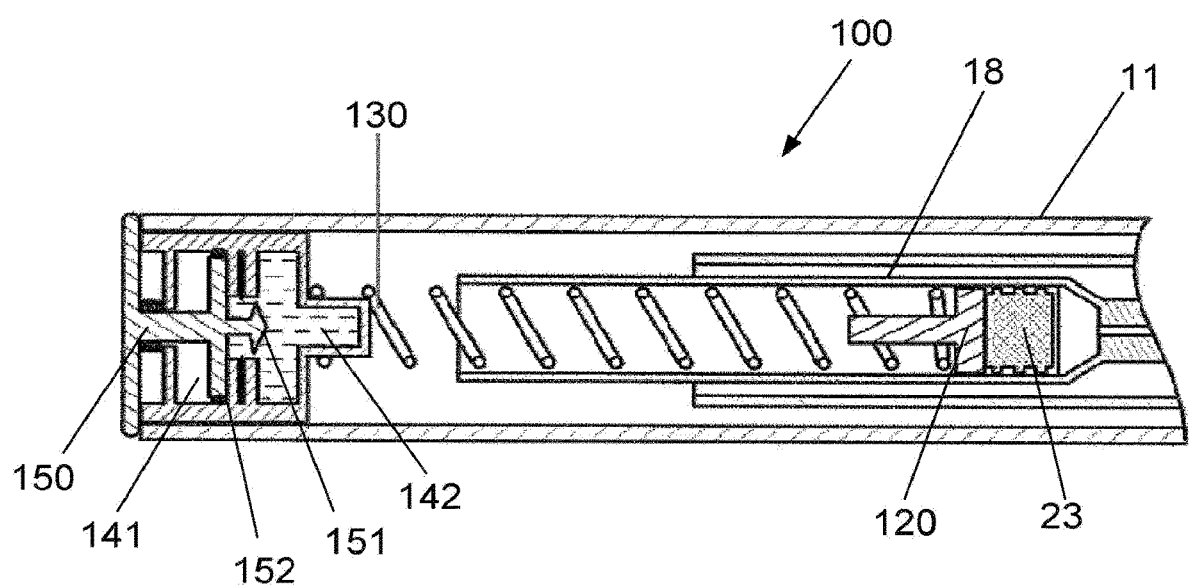
FIG. 4 is a schematic cross-sectional side view of the auto-injector device of FIG. 2.

FIG. 4 shows the injection device 100 of the first embodiment in a final state. The temperature of the driving element 130 is raised above the threshold, such that the driving element 130 changes from the first configuration to the second configuration. The expanded coil shape of the second configuration has a greater length than the compressed coil shape of the first configuration and so the driving element 130 exerts an axial force of the piston 120 as it expands. The rubber stopper 23 of the syringe 18 is displaced by the piston 120 towards the distal end of the medicament chamber, which causes the medicament to be dispensed through the needle of the syringe 18.

The first embodiment provides an improved driving element for an auto-injector device and, in addition, the mechanism of the dispense mechanism can aid with warming the medicament prior to injection. By warming the medicament to be closer to the body temperature of the user, prior to injection, the comfort of the user can be improved. The exothermic chemical reaction may be an exothermic neutralisation reaction between an acid and a base, for example, between citric acid and sodium hydroxide.

In an alternative embodiment, the heating mechanism comprises a single chemical fluid which is contained in a chamber. The location and form of the chamber is substantially as described with respect to the second chamber above. The piercing element comprises an activation surface which triggers an exothermic process in the chemical fluid when the chemical fluid makes contact with the activation surface. The dispense button is configured to push the piercing element with the activation surface into the second chamber through the frangible membrane, which causes the generation of heat from the exothermic process.

The chemical contained in the chamber is a supersaturated solution of, for example, sodium acetate trihydrate. The activation surface triggers an exothermic crystallisation process in the supersaturated solution. This heating mechanism provides a rechargeable energy source which can generate heat through multiple phase changes, when the supersaturated solution is reformed under the influence of heat followed by gentle cooling. The dispense mechanism according to the embodiment can therefore be implemented as part of a reusable device.

Figure 5:
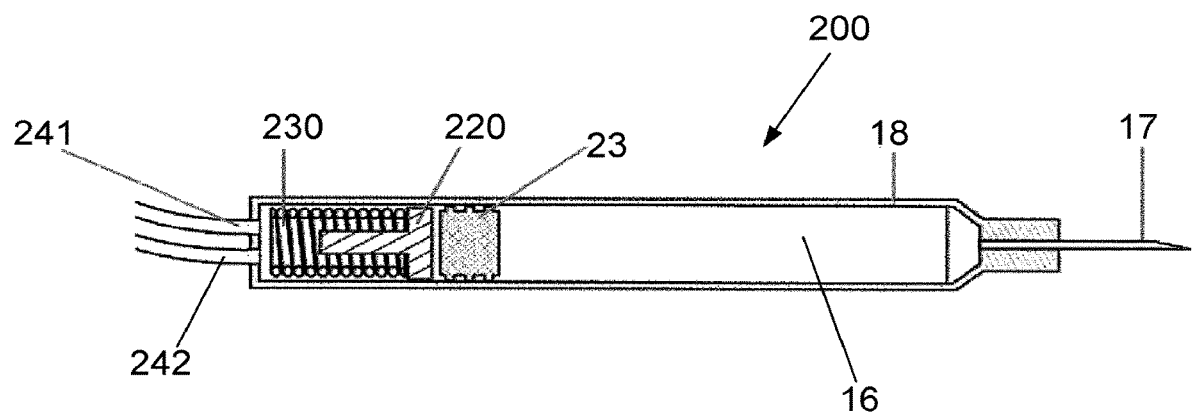
FIG. 5 is a schematic cross-sectional side view of the FIGS. 1A and 1B auto-injector device according to an exemplary embodiment.

With reference to FIG. 5, an injection device 200 according to a second embodiment is described. Elements of the embodiment which are not described are substantially the same as those of the first embodiment.

The dispense mechanism 210 comprises a piston 220, a driving element 230 and a heating mechanism 240. The piston 220 is coupled to the rubber stopper 23 of the syringe 18, and the driving element 230 is disposed within the syringe 18 between the piston 220 and the proximal end of the medicament chamber.

The driving element 230 is formed from a SMA, substantially as described with respect to the first embodiment. The SMA forms a driving element 230 having a first configuration, which is a compressed coil shape, and a second configuration, which is an expanded coil shape. The expanded coil shape of the second configuration has a greater length than the compressed coil shape of the first configuration.

When the temperature of the driving element 230 rises above the threshold the shape of the driving element 230 changes from a compressed coil shape to an expanded coil shape and therefore the length of the driving element 230 increases. The expansion of the driving element 230 exerts an axial force on the piston 220, which displaces the rubber stopper 23 of the syringe 18 towards the distal end of the medicament chamber. The change in configuration of the driving element 230 therefore causes the medicament 16 to be dispensed through the needle 17 of the syringe 18.

The heating mechanism 240 of the dispense mechanism 220 is configured to raise the temperature of the driving element 230 when the dispense mechanism 220 is activated. The heating mechanism 240 comprises a fluid reservoir, a heater and a pump disposed in an external device (not shown), and a connecting tube 241 arranged to connect the fluid reservoir with the proximal end of the medicament chamber. The temperature of the driving element 230 is raised when a heated fluid 243, or gas, enters the proximal end of the medicament chamber through the connecting tube 241. The driving element 230 is immersed in the heated fluid 243, which improves the rate at which the temperature of the driving element 230 is raised.

The fluid 243 or, alternatively, the gas, for heating the driving element 230 is stored in the fluid reservoir and heated by the heater in the external device. When the dispense mechanism is activated, the pump forces the heated fluid 243 through the connecting tube 241 into the proximal end of the medicament chamber. A return tube 242 allows the heated fluid 243 to flow back to the external device, whereby the circulation of the heated fluid 243 improves the rate at which the temperature of the driving element 230 is raised.

Figure 6:
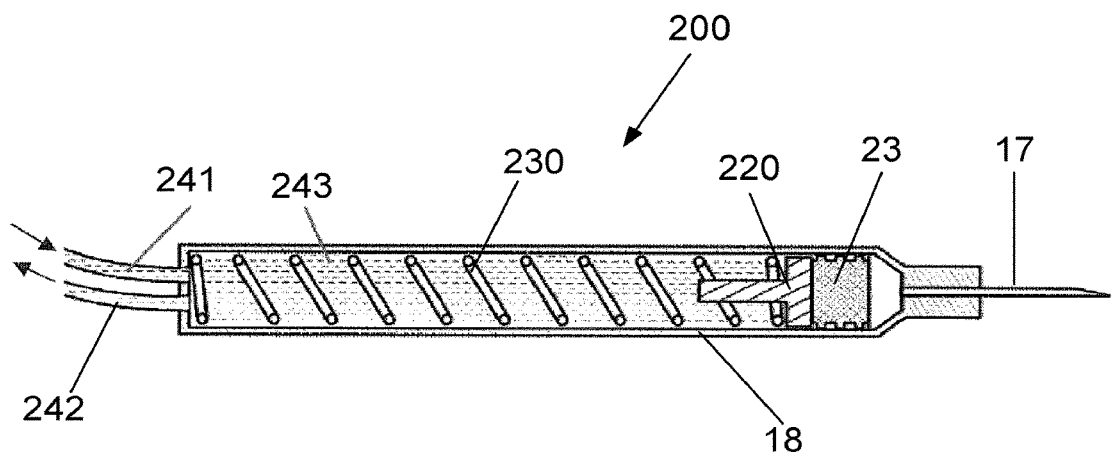
FIG. 6 is a schematic cross-sectional side view of the auto-injector device of FIG. 5.

FIG. 6 shows the injection device 200 of the second embodiment in an activated state. The driving element 230 is immersed in the heated fluid 243, and the temperature of the driving element 230 is raised above the threshold, such that the driving element 230 changes from the first configuration to the second configuration. The expanded coil shape of the second configuration has a greater length than the compressed coil shape of the first configuration and so the driving element 230 exerts an axial force of the piston 220 as it expands. The rubber stopper 23 of the syringe 18 is displaced by the piston 220 towards the proximal end of the medicament chamber, which causes the medicament to be dispensed through the needle 17 of the syringe 18.

Although FIG. 5 and FIG. 6 depict an injection device 200 comprising the syringe 18 and dispense mechanism 210 only, the dispense mechanism 210 of the second embodiment may be implemented as part of an injection device having a housing and any other parts described with respect to FIGS. 1 to 4.

The second embodiment can therefore provide an improved driving element for an auto-injector device and, in addition, the mechanism of the dispense mechanism can aid with warming the medicament prior to injection. By warming the medicament to be closer to the body temperature of the user, prior to injection, the comfort of the user can be improved.

Although a few embodiments have been shown and described, it will be appreciated by those skilled in the art that changes may be made in these embodiments without departing from the invention, the scope of which is defined in the appended claims. Various components of different embodiments may be combined where the principles underlying the embodiments are compatible. For example, the chemicals of the first embodiment may be any suitable chemicals which can be combined to produce heat in an exothermic process, and may be in a solid, liquid or gas form.

In some embodiments, the first chemical may be powdered calcium oxide or quicklime and the second chemical is water, and the combination of the first and second chemicals generates heat from an exothermic chemical reaction forming a calcium hydroxide solution. Alternatively, the first chemical may be a dehydrated salt such as calcium chloride or copper (II) sulphate and the second chemical is water, wherein the heating mechanism is an exothermic rehydration process.

The driving element of any embodiment may be formed as a coiled spring, as described, or may be formed as a flat folded spring, e.g. a concertina shape, which expands when the temperature of the driving element is raised above the threshold.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, microneedle), inhaler (e.g., nasal or pulmonary), an implantable device (e.g., drug- or API-coated stent, capsule), or a feeding system for the gastro-intestinal tract. The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyhepta-¬decanoyl) human insulin.

Examples of GLP-1, GLP-1 analogues and GLP-1 receptor agonists are, for example, Lixisenatide (Lyxumia®, Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a polysulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

The invention claimed is:

1. An auto-injector device comprising:
a medicament reservoir;
a stopper for expelling a medicament out of the medicament reservoir;
a driving element, formed from a shape memory alloy, which has a first configuration and a second configuration and is configured to change shape from the first configuration to the second configuration when a temperature of the driving element is raised above a shape change temperature, so as to drive the stopper through the medicament reservoir; and
a heating mechanism configured to actively heat the driving element, wherein the heating mechanism is a chemical heating element configured to generate heat through an exothermic process, wherein the exothermic process is an exothermic chemical reaction between a first chemical and a second chemical, wherein the heating mechanism comprises:
a first chamber containing the first chemical;
a second chamber containing the second chemical and connected to the first chamber by an aperture;
a frangible membrane arranged across the aperture to separate the first chamber and the second chamber; and
a piercing element configured to be displaced through the first chamber to pierce the membrane to initiate the exothermic chemical reaction.

2. The auto-injector device of claim 1, wherein the first configuration of the driving element is a compressed coil shape, and the second configuration of the driving element is an expanded coil shape.

3. The auto-injector device of claim 1, wherein the shape memory alloy is a nickel-titanium alloy.

4. The auto-injector device of claim 1, further comprising a medicament which is retained in the medicament reservoir and is arranged to be expelled from the medicament reservoir by the stopper.

5. The auto-injector device of claim 1, wherein the second chamber comprises a protruding portion at a distal end of the second chamber.

6. The auto-injector device of claim 5, wherein the protruding portion extends into a central region of the driving element.

7. The auto-injector device of claim 1, wherein the second chamber comprises a metallic or ceramic material.

8. The auto-injector device of claim 1, wherein a distal end of the driving element is mechanically coupled to a shoulder of the stopper.

9. A method of operating an injection device, comprising:
heating a driving element formed from a shape memory alloy, using a heating mechanism configured to generate heat through an exothermic process, wherein the exothermic process is an exothermic chemical reaction between a first chemical and a second chemical,
wherein the driving element has a first configuration and a second configuration and is configured to change shape from the first configuration to the second configuration when a temperature of the driving element is raised above a shape change temperature, so as to drive a stopper through a medicament reservoir and expel a medicament out of the medicament reservoir,
wherein the heating mechanism comprises:
a first chamber containing the first chemical;
a second chamber containing the second chemical and connected to the first chamber by an aperture;
a frangible membrane arranged across the aperture to separate the first chamber and the second chamber; and
a piercing element configured to be displaced through the first chamber to pierce the membrane to initiate the exothermic chemical reaction.

10. The method of claim 9, wherein heating the driving element comprises causing the driving element to lengthen.

11. The method of claim 9, wherein heating the driving element comprises heating the driving element in response to activation of a dispense mechanism of the injection device.

12. The method of claim 9, wherein the first configuration of the driving element is a compressed coil shape, and the second configuration of the driving element is an expanded coil shape.

13. The method of claim 9, wherein the shape memory alloy is a nickel-titanium alloy.

14. The method of claim 9, wherein the second chamber comprises a protruding portion at a distal end of the second chamber.

15. The method of claim 14, wherein the protruding portion extends into a central region of the driving element.

16. The method of claim 9, wherein the second chamber comprises a metallic or ceramic material.

17. The method of claim 9, wherein a distal end of the driving element is mechanically coupled to a shoulder of the stopper.

18. An auto-injector device comprising:
a medicament reservoir;
a stopper for expelling a medicament out of the medicament reservoir;
a driving element, formed from a shape memory alloy, which has a first configuration and a second configuration and is configured to change shape from the first configuration to the second configuration when a temperature of the driving element is raised above a shape change temperature, so as to drive the stopper through the medicament reservoir;
a heating mechanism configured to actively heat the driving element, wherein the heating mechanism is a chemical heating element configured to generate heat through an exothermic process, wherein the exothermic process is an exothermic crystallization of a supersaturated solution and
an element comprising an activation surface for triggering the exothermic process when the activation surface contacts with the supersaturated solution, wherein the element is configured to be displaced to cause the activation surface contacting with the supersaturated solution to trigger the exothermic process.

19. The auto-injector device of claim 18, wherein the shape memory alloy is a nickel-titanium alloy.

20. The auto-injector device of claim 18, wherein the heating mechanism includes a chamber to contain the supersaturated solution, the chamber comprising a protruding portion at a distal end of the chamber.

* * * * *

UNITED STATES PATENT AND TRADEMARK OFFICE
CERTIFICATE OF CORRECTION

PATENT NO. : 11,752,264 B2
APPLICATION NO. : 17/099707
DATED : September 12, 2023
INVENTOR(S) : Stefan Wendland and Michael Harms It is certified that error appears in the above-identified patent and that said Letters Patent is hereby corrected as shown below:

In the Claims

Column 13, Line 54, Claim 9, delete "inj ection" and insert -- injection --

Signed and Sealed this
Thirty-first Day of October, 2023

Katherine Kelly Vidal
*Director of the United States Patent and Trademark Office*